United States Patent
Holmberg et al.

(10) Patent No.: US 11,007,140 B2
(45) Date of Patent: May 18, 2021

(54) METHOD FOR MANUFACTURING A DRUG DELIVERY DEVICE AND A DRUG DELIVERY DEVICE MANUFACTURED ACCORDING TO THE METHOD

(71) Applicant: BAYER OY, Turku (FI)

(72) Inventors: Svante Holmberg, Turku (FI); Heikki Lyytikäinen, Naantali (FI); Christine Talling, Turku (FI); Saara Ruotsalainen, Lappeenranta (FI); Petri Laakso, Lappeenranta (FI)

(73) Assignee: Bayer OY, Turku (FI)

( * ) Notice: Subject to any disclaimer, the term of this patent is extended or adjusted under 35 U.S.C. 154(b) by 0 days.

(21) Appl. No.: 16/064,503

(22) PCT Filed: Dec. 19, 2016

(86) PCT No.: PCT/EP2016/081715
§ 371 (c)(1),
(2) Date: Jun. 21, 2018

(87) PCT Pub. No.: WO2017/108676
PCT Pub. Date: Jun. 29, 2017

(65) Prior Publication Data
US 2019/0000751 A1    Jan. 3, 2019

(30) Foreign Application Priority Data
Dec. 21, 2015   (EP) .................................... 15201533

(51) Int. Cl.
*A61K 9/00*        (2006.01)
*A61K 31/4196*     (2006.01)
*A61K 31/567*      (2006.01)
*A61K 31/00*       (2006.01)

(52) U.S. Cl.
CPC ............ *A61K 9/0036* (2013.01); *A61K 31/00* (2013.01); *A61K 31/4196* (2013.01); *A61K 31/567* (2013.01)

(58) Field of Classification Search
None
See application file for complete search history.

(56) References Cited

U.S. PATENT DOCUMENTS

| | | | | |
|---|---|---|---|---|
| 4,292,965 A | * | 10/1981 | Nash | A61K 9/0036 128/833 |
| 6,846,852 B2 | * | 1/2005 | Allen | C08G 77/20 522/109 |
| 8,980,304 B2 | * | 3/2015 | Tsao | A61K 9/0036 424/430 |
| 9,937,335 B2 | * | 4/2018 | Moss | A61K 9/0036 |
| 2011/0146693 A1 | * | 6/2011 | Duesterberg | A61K 9/0039 128/833 |
| 2011/0208135 A1 | * | 8/2011 | Hakala | A61K 9/0034 604/285 |
| 2012/0057219 A1 | * | 3/2012 | Suyama | G03B 33/12 359/328 |
| 2013/0131027 A1 | * | 5/2013 | Pakkalin | A61K 9/0036 514/171 |
| 2015/0224200 A1 | * | 8/2015 | de Juan, Jr. | A61K 31/215 424/427 |
| 2017/0168261 A1 | * | 6/2017 | Itami | G01S 7/4817 |

FOREIGN PATENT DOCUMENTS

WO    2010/133757    11/2010

OTHER PUBLICATIONS

Tavakoli "The Adhesive Bonding of Medical Devices" 2001.*
Kiser et al. "State of the Art in Intravaginal Ring Technology for Typical Prophylaxis of HIV Infection". 2012.*
Winder D.J. (2008) Computer Assisted Cranioplasty. In: Bidanda B., Bártolo P. (eds) Virtual Prototyping & Bio Manufacturing in Medical Applications. Springer, Boston, MA . https://link.springer.com/content/pdf/10.1007%2F978-0-387-68831-2.pdf.*
IRphotonics "Controlling Heat Curing Adhesive Process Using Infrared Spot Curing" 2012.*
International Search Report for PCT/EP2016/081715 dated Mar. 1, 2017, 2 pages.

* cited by examiner

Primary Examiner — Danah Al-Awadi
(74) Attorney, Agent, or Firm — McBee Moore & Vanik IP, LLC

(57) ABSTRACT

The invention relates to a method for producing a drug delivery device, which has a body comprising a siloxane-based elastomer and at least one active agent. The method comprises applying adhesive material, which comprises non-cured siloxane based elastomer, into a contact with the body and curing the said adhesive material by subjecting it to radiation energy from a laser source. The invention relates also to a drug delivery device manufactured according to the method.

16 Claims, 2 Drawing Sheets

METHOD FOR MANUFACTURING A DRUG DELIVERY DEVICE AND A DRUG DELIVERY DEVICE MANUFACTURED ACCORDING TO THE METHOD

This application is the U.S. national phase of International Application No. PCT/EP2016/081715 filed Dec. 19, 2016 which designated the U.S. and claims priority to EP Patent Application No. 15201533.5 filed Dec. 21, 2015, the entire contents of each of which are hereby incorporated by reference.

The present invention relates to a method for manufacturing a drug delivery device, in particular an intravaginal ring or an implant, according to the preamble of the enclosed independent claim. The invention further relates to a drug delivery device manufactured according to the method.

TECHNICAL FIELD

A use of drug delivery devices is advantageous in many therapeutic areas. These devices provide a slow release of a drug to the human or animal body at a controlled rate over a prolonged period of time in order to achieve a desired physiological or pharmacological effect. Besides improved patient compliance one of the benefits of employing sustained-release compositions is also that many therapeutically active agents would otherwise be rapidly metabolised or cleared from the human system, which would require frequent administration of the active agent to maintain a therapeutically effective dosage level.

Elastomer materials, which are suitable for use in drug delivery devices, are known. In general, suitable alternatives for drug delivery devices are thermoplastic polymers, such as ethylene vinyl acetate (EVA); elastomeric silicones, such as polysiloxanes; as well as biodegradable polymers, such as polylactic acids.

Drug delivery devices comprising a thermosetting elastomer-based body, which may comprise a core and/or membrane, are known. For example, polysiloxanes, such as poly(dimethylsiloxane), PDMS, are suitable for use in device bodies as membrane material and/or core material. Polysiloxanes are physiologically inert, and a wide group of active agents are capable of penetrating polysiloxane membranes, which also have the required mechanical properties. Typical examples of these kinds of drug delivery devices are implants and various intrauterine systems (IUS).

Many of the drug delivery device bodies comprise an elastomer matrix or core, which contains active agent(s). The core is often covered by a membrane, which regulates the permeation of the active agent(s) and ensures a constant and controlled, usually slow, delivery rate over the lifetime of the device.

Sometimes there is a need for attachment of different elastomer-based parts in manufacture of drug delivery devices. For example, in production of intravaginal rings, the ring-like device is usually assembled from a plurality of cores. Some of the cores comprise active agent(s), whereas some of the cores are drug-free and added to the device mainly for achieving an adequate size of the ring to ensure a stable fit in the vaginal cavity. Alternatively the drug delivery device may comprise a plurality of different active agents, each active agent being present and embedded in its own part. The final drug delivery device is then produced by assembling the individual parts in desired order and attaching the pre-assembled parts together.

It is possible to attach the elastomer-based parts together by using a silicon based adhesive material between the individual parts to be attached. Alternatively the parts can be inserted into a membrane tube, which surrounds them and holds them together in a rod-like form without adhesive material. However, even when the attachment of the individual parts is accomplished by the membrane tube, for formation of a ring-like structure, the ends of the pre-assembled rod-like structure are still attached together by using silicon based adhesive material.

Usually silicone adhesive materials are cured by applying heat or moisture. However, some active agents used in drug delivery devices are sensitive to elevated temperatures. This means that after the active agent is incorporated into the elastomer-based matrix of the device body, the body cannot be subjected to treatment at elevated temperatures. But even if the active agent as such would be stable at elevated temperature without degradation, heating is preferably avoided in production of drug delivery devices, especially with active agents having a low melting point. In that case the active agent usually exists in a microcrystalline form, which is dispersed in the polymer matrix of the body. Subjecting these microcrystals to heating might cause at least partial melting of the active agent. Melting of the active agent impacts the release kinetics and should be avoided.

Silicone adhesive material may be self-curing without any heat-treatment. Such self-curing silicone adhesives usually contain a catalyst, e.g. metal catalyst, and/or cure when subjected to the moisture in the air. The curing of self-curing silicone adhesives normally require a curing time of at least 24 hours until the required mechanical strength is obtained. This easily forms a bottle-neck in the production process, and is not feasible in industrial scale.

In some drug delivery devices it would be advantageous if only a well-restricted area of the device body could be cured. For example, restricted curing of a part of the device body could be used for sealing the ends of an implant or the open ends of a drug containing capsule as used in intrauterine systems (IUS).

In view of the above, there exists a need for a method with which a fast attachment of elastomer-based parts of a drug delivery device can be obtained. The method should be suitable for automation and fulfil requirements for manufacture of drug delivery devices in cleanroom environment.

Furthermore, there exists a need for a method which would minimize the risk of subjecting the active agent to heat stress, in order to avoid degradation or melting of the active agent.

SUMMARY AND OBJECT OF THE INVENTION

An object of this invention is to minimise or possibly even eliminate the disadvantages existing in the prior art.

Another object of the present invention is to provide a fast and effective process for producing a drug delivery device.

A further object of the present invention is to avoid heat exposure of the whole drug delivery device during curing of adhesive agent.

These objects are attained with the invention having the characteristics presented below in the characterising parts of the independent claims.

Some preferable embodiments of the invention are presented in the dependent claims. The features recited in the dependent claims are freely combinable with each other unless otherwise explicitly stated.

Typical method according to the present invention for producing a drug delivery device, which has a body comprising a siloxane-based elastomer and at least one therapeutically active agent, the method comprises applying adhesive material, which comprises non-cured siloxane based elastomer, into a contact with the body and curing the said adhesive material by subjecting it to radiation energy from a laser source.

DETAILED DESCRIPTION OF THE INVENTION

Figure 1:
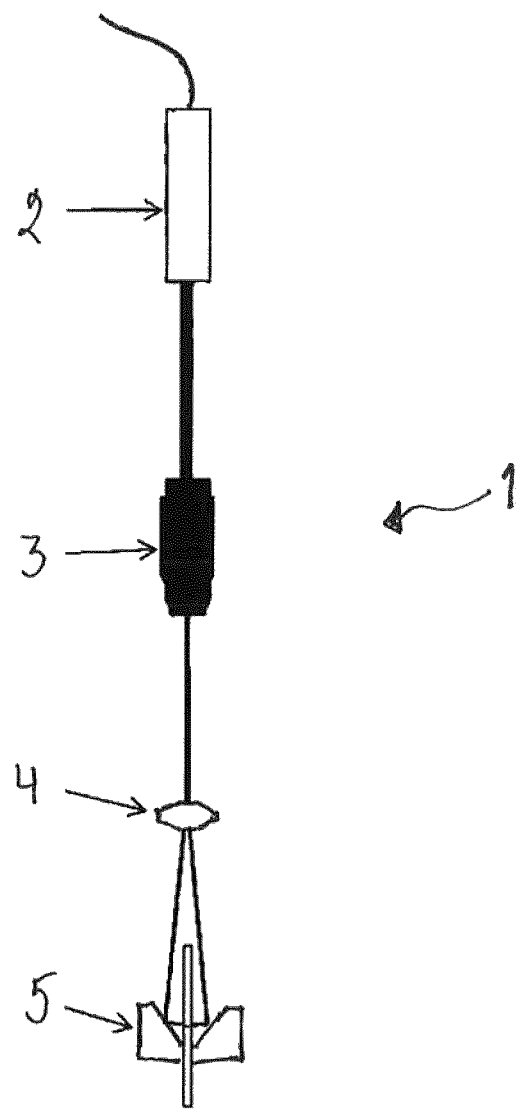
FIG. 1 is a schematic view of an example embodiment of an optical setup for guiding a laser beam.

Typical method according to the present invention for producing a drug delivery device, which has a body comprising a siloxane-based elastomer and at least one active agent, comprises applying adhesive material, which comprises non-cured siloxane based elastomer, into a contact with the body and curing the said adhesive material by subjecting it to radiation energy from a laser source.

The embodiments mentioned in this text relate, where applicable, to all aspects of the invention, i.e. both the method and device, even if this is not always separately mentioned.

In the present context the term "drug delivery device" encompasses intrauterine systems, implants and intravaginal rings that contain one or more active agents, for example contraceptive agents, and/or one or more therapeutically active agents.

In the present context it is understood that the drug delivery device comprises a body, which can either be made of one single part or comprise a plurality of body parts, which are connected or attached to each other in order to form the body. The body of the drug delivery device may preferably comprise a core and a membrane enclosing the core.

In the present context it is understood that an individual body part may either comprise only a core or a core and a membrane enclosing the said core.

In the present context it is understood that a core comprise a solid elastomer-based material or matrix. The material or matrix may comprise an active agent or be free of active agent(s). A core can be made of one single piece or a plurality of individual parts.

In the present context it is understood that a membrane is arranged to enclose or surround the core. The membrane may be an elastomer based tube, which covers the surface of the core. The membrane usually regulates the release of the active agent(s) from the core to the surrounding environment.

In the present context the term "silicon based adhesive material" is understood as uncured silicone based elastomer. The term is synonymous to terms "adhesive material", "adhesive", "adhesive agent" or "glue", and these terms are used interchangeably. When one is mentioned the others are also covered.

In the present context the term "curing" is understood as a process where the temperature of adhesive material comprising uncured siloxane based elastomer is increased and the polymeric chains of the adhesive material are crosslinking with each other. Curing is thus a chemical reaction, where uncured siloxane based elastomer is cross-linked, the cross-linking reaction being initiated by radiation from a laser source. For example, the cross-linking may be a result of a process initiated by radicals formed by the temperature increase in the adhesive material. Curing in the sense of the present context is thus essentially different from e.g. heat welding process, where a thermoplastic material is melted. During curing the adhesive material is free of melting, i.e. the polymer chains of the adhesive agent retain their length.

The present invention is especially suitable for use in drug delivery devices comprising siloxane-based elastomer(s). Siloxane-based elastomers cannot be connected or attached by using heat welding, as the elastomers do not melt at elevated temperature. Therefore the present invention provides unexpected possibilities in improving the effectivity of production process of drug delivery devices comprising siloxane-based elastomer(s).

Now it has been surprisingly found that an adhesive material comprising non-cured siloxane based elastomer can be cured in a fast and efficient manner by using radiation energy from a laser source. The adhesive material is arranged into the contact with the body or between body parts of the drug delivery device and cured with laser radiation. The radiation energy penetrates into the adhesive material and energy is absorbed by the adhesive material. The radiation energy absorbed by the adhesive material is at least partially transformed into heat energy in a sharply focused area which comprises the adhesive material. Thus the radiation energy from a laser source produces localized heat increase, which is focused on the delimited area comprising the adhesive material. It is assumed, without wishing to be bound by a theory that the localized heat increase induces curing of the uncured adhesive material by radical formation and following radical initiation. The radiation energy from the laser source can be carefully targeted and sharply focused to the adhesive material and any unnecessary heating of the whole drug delivery device can be avoided. In other words the heat is not spread from the connection comprising the adhesive material to the whole body of the drug delivery device. Thus the possible active agents and/or therapeutically active agent(s) embedded in the body of the drug delivery device are not changed, melted and/or destroyed by heat. The method according to invention is especially suitable for producing implants and intravaginal rings.

The curing of the adhesive material by radiation energy from the laser source is a fast process. Typically the adhesive material needs to be subjected to the radiation energy only for milliseconds up to seconds. The adhesive material may be subjected for laser radiation less than one second and up to five seconds in order to provide the curing of the adhesive material, According to one embodiment the exposure time for laser radiation may be, for example, 0.2-5 s, preferably 0.5-3 s, more preferably 0.7-2 s. After the short exposure to radiation from the laser source a strong permanent connection is formed, e.g. between the ends of the elongated rod-like body or between adjacent body parts as explained later in this application. It is clear that the curing of the adhesive material by laser radiation makes the manufacture of drug delivery device fast and effective. Furthermore, the radiation energy from the laser source, which is focused on the area of the connection, preserves the (therapeutically) active agent(s) included in the body of the drug delivery device.

The radiation energy from the laser source has a penetration depth which is sufficient to ensure curing of the adhesive material not only on the surface, but over the whole thickness of the adhesive material. This means that preferably the applied adhesive material is wholly and completely cured. The adhesive material is thus preferably cured over the whole cross-section of the connection, and the adhesive material adsorbs the radiation energy throughout the whole of its thickness. This provides a strong connection between the ends of the body or adjacent body parts.

According to one embodiment of the invention the radiation energy from the laser source increases the temperature in the adhesive material to be cured to a temperature of at least 150° C., preferably at least 200° C. The temperature in the adhesive material can be increased to a temperature in the range of 150-300° C., preferably 200-270° C., more preferably 220-260° C. This short and effective temperature increase induces the curing of the adhesive material without causing any negative effects, such as degradation or spreading of the heat outside the connection.

The controlled heat increase which is produced by the radiation energy from the laser source speeds up the curing reactions of the adhesive material comprising siloxane-based elastomer. Thus the overall process time for curing can be shortened.

The suitable laser source may be selected by determining the absorption profile of the adhesive material. After that an absorption maximum of the adhesive material is determined, and a laser source having a wavelength near the said absorption maximum, e.g. around 30-60% of the absorption maximum, is selected for curing. In this manner an effective absorption of the radiation energy by the adhesive material can be guaranteed without destroying the structure of adhesive material. This provides the satisfactory curing speed and efficiency.

According to one embodiment of the invention the laser source may produce radiation energy having a wavelength in the range of 1100-2000 nm. According to one embodiment the laser source may produce radiation energy having a wavelength of 1940 nm. According to other embodiment the laser source is a continuous wave thulium laser with a wavelength of 1940 nm. According to yet another embodiment the laser source can be a continuous wave erbium laser with a wavelength of 1550 nm. These laser sources provide good results especially when the adhesive material is poly(dimethylsiloxane).

The laser source may comprise a diode laser, where the laser light is produced in multiple semiconductors arranged in a row. Multiple of these semiconductor rows can be arranged in a stack in order to increase the power level achieved.

The output power of the laser may be in the range of 20-200 W, preferably 50-150 W.

Scanning speed of the laser may be optimised in order to obtain proper curing of the adhesive material and thus a connection with good strength properties. It has been observed that a fast scanning speed and short exposure time is advantageous for achieving a more uniform and sensitive heat effect, which produces good curing and high material strength for the adhesive material. At the same time any negative effects, such as degradation of the adhesive material, is avoided. A person skilled in the art can optimise the scanning speed with few simple experiments.

Various optical setups can be arranged for guiding, positioning, focusing and controlling the radiation energy from the laser source. For example, with a diffractive optical element system it is possible to illuminate the whole area where the adhesive agent is applied at one time.

The adhesive material, which is suitable for use in the present invention, may be any uncured conventional adhesive material comprising siloxane-based elastomer, suitable for (therapeutical) applications for mammals, especially humans. The adhesive may be an uncured polysiloxane or a modified polysiloxane adhesive, which is substituted with functional groups, such as fluoropropyl or poly(ethylene oxide) groups. The adhesive material typically comprises furthermore a platinum catalyst or a peroxide initiator. Uncured adhesive material contains cross-linkable groups, such as vinyl or vinyl-terminated groups, and is essentially free of cross-linking.

According to one preferable embodiment of the present invention the adhesive material is uncured siloxane-based elastomer, which is selected from the same group of siloxane-based elastomers, which are used for the manufacture of the body or body parts of the drug delivery device. Suitable elastomers are disclosed later in this application in connection with body/body parts. Even more preferably the adhesive agent is the same siloxane-based elastomer that is used in the body or one of the body parts of the drug delivery device, in the core and/or the membrane of the drug delivery device. Thus a strong connection can be obtained by using the same elastomer which already exists in the drug delivery device, and no foreign components or compounds need to be used. This is naturally advantageous in manufacture of drug delivery devices, in particular in view of the regulatory approval processes, where otherwise additional toxicological data may be required in case the adhesive agent differs from the body material.

The adhesive material may comprise a peroxide initiator, which forms radicals when subjected to radiation energy from the laser source. One possible peroxide initiator, which may be incorporated into the adhesive material is 2,4-dichlorobenzoyl peroxide. The 2,4-dichlorobenzoyl peroxide decomposes by heat, whereby only minimal insignificant traces, if any at all, of initiator is present in the final drug delivery device. Preferably, no initiator can be observed in the connection of the final drug delivery device. Other examples of suitable organic peroxide initiators for cross-linking of the adhesive material are bis(2,4-dichlorobenzoyl) peroxide, dicumyl peroxide, di-tert-butyl peroxide, dibenzoyl peroxide, tert-butyl benzoate, bis(4-methylbenzoyl) peroxide, bis(o-monochlorobenzoyl) peroxide, bis(p-monochlorobenzoyl) peroxide, 2,5-dimethyl-2,5-di(tertbutylperoxy) hexane, 1,1-bis(tert-butylperoxy)-3,3,5-trimethylcyclohexane, 1,6-bis(tert-butyl-peroxycarboxy) hexane and 1,4-bis-(tert-butylperoxyisopropoxy) benzene.

Alternatively, the adhesive material may comprise a noble metal catalyst, such as platina.

In general, condensation curing silicones are not suitable as adhesive material in the present invention.

Alternatively, in some embodiments the adhesive material may be free from noble metal catalyst, such as platina. When noble metal catalyst is not needed, the production costs can be reduced. Furthermore, no noble metal residues remain in the final drug delivery device.

The connection which is formed by curing the adhesive material by laser radiation, for example between the ends of the body or between adjacent body parts, may have a tensile strength of at least 12 N, preferably at least 40 N, more preferably at least 45 N, even more preferably at least 50 N. The tensile strength values can be measured by using Lloyd Instrument LR5KPlus 5 kN Universal Materials Testing Machine TL14002, testing speed 40 mm/min. Preferably a strong connection is maintained for a minimum of 5 years.

According to one embodiment of the invention the adhesive material is applied between the ends of the body or between adjacent body parts in amount that provides preferably a connection with a width of up to 5 mm, more preferably less than 1 mm. The connection width may be in the range of 0.1-15 mm, preferably 0.5-10 mm, more preferably 0.5-1.5 mm.

After application of the adhesive material, but before curing, any surplus adhesive material is removed, whereby the surface of the drug delivery device remains smooth and flat also over the connection between the ends of the elongated body or between adjacent body parts.

According to one embodiment of the present invention the drug delivery device may comprise at least one connection, formed by the adhesive material, which connection attaches two adjacent body parts irrevocably together after curing with laser radiation. This means that the drug delivery device is produced by forming the body of the device by applying the adhesive material between a first siloxane-based elastomer body part and a second siloxane-based elastomer body part, whereby the adhesive material forms an immediate connection between the first body part and the second adjacent body part, and attaches them irrevocably together after curing. The adhesive material may also be applied between any further successive body parts, forming an immediate and irrevocable connection between these body parts after curing. The body of the drug delivery device is thus formed from at least two, preferably a plurality of, body parts which have been attached irrevocably together with a connection formed of adhesive material cured by radiation from laser source.

The first, second and any successive adjacent body part comprises siloxane-based elastomer and optionally at least one active agent incorporated into the said elastomer. The first, second and any successive adjacent body part may comprise a core and a membrane enclosing the said core. Alternatively, each adjacent body part may comprise only a core and be free of membrane enclosing the core. In the latter case the body parts, i.e. cores, are then attached together with adhesive material before a membrane is arranged to enclose them.

The core and/or membrane of the adjacent body parts may be different chemically and/or physically from each other, and they may contain different active agents.

For example, the core, the optional membrane as well as the optional active agent may be same or different in the first, second and any successive body parts. If required, some of the body parts may be free of active agent(s).

According to another embodiment of the invention the drug delivery device is a ring-like drug delivery device, which comprises at least one connection, possibly several connections, which are formed by the adhesive material. The ring-like device may be produced by applying the adhesive material between a first end and a second end of the body of the drug delivery device, whereby the adhesive agent forms an immediate connection between the first end and the second end of the body and attaches them irrevocably together after curing with radiation from laser source. In this manner a ring-like drug delivery device, such as intravaginal ring, can be easily formed.

According to one preferable embodiment the ring-like drug delivery device is produced by obtaining an elongated body and forming the elongated rod-like body into a ring-like form by bringing its first end and the second end into close vicinity of each other. The adhesive material is arranged between the first end and second end of the body, whereby the adhesive material is cured by subjecting it to radiation energy from the laser source and the ends are irrevocably attached together. The ends of the elongated body are connected to each other via the connection formed from the cured adhesive material The elongated rod-like body from which the ring-like drug delivery device is formed may comprise a plurality of body parts, which are attached together with the adhesive material. The individual body parts may comprise a core and a membrane enclosing the said core.

According to another embodiment the ring-like drug delivery device may be produced from an elongated rod-like body, which comprises a plurality of body parts which have been assembled into a membrane tube, which surrounds the body parts and holds the parts in a rod-like form. The pre-assembled body parts may be attached to each other with adhesive material cured by laser radiation to form a core of the device. A membrane may then be arranged to enclose the formed core. Insertion of the core into the membrane may occur either by swelling a membrane tube in a suitable solvent, insertion of the core into the swelled membrane tube and subsequent removal of the solvent or by expanding a membrane tube either with vacuum or pressurized air before the insertion of the core into the membrane tube.

Alternatively, the elongated rod-like body which is formed into a ring-like device may comprise a plurality of core parts, which are hold together by the surrounding membrane only, without any adhesive material between the adjacent core parts. The elongated body is then formed into a ring-like drug delivery device by attaching the first end and the second end of the elongated body irrevocably together with adhesive material cured with radiation energy from a laser source.

Alternatively, the elongated rod-like body may comprise a single core, enclosed by a surrounding membrane as described above. The ring-like drug delivery device is formed by attaching the first end and the second end of the body irrevocably together with adhesive material cured with radiation energy from a laser source.

In the above described embodiments the core and/or membrane of the individual body parts of the ring-like device may be different chemically and/or physically from each other, and they may contain different active agents. For example, the core, the optional membrane as well as the optional active agent may be same or different in the first, second and any successive body parts.

When the intravaginal ring comprises a plurality of body parts, some of the body parts may comprise active agent and some of the body parts may be free of active agent. These latter inactive body parts are used to give the ring a sufficient size to ensure a stable anchoring in the vagina.

According to one preferable embodiment of the invention the drug delivery device is an intravaginal ring. Such intravaginal rings have a body that comprise at least one core formed from thermosetting siloxane-based elastomer matrix, such as PDMS, as well as a membrane enclosing the core(s). The body of the intravaginal ring, which comprises the core and the membrane, may be produced in any manner described in the preceding paragraphs, which relate to ring-like drug delivery devices. At least one of the cores or body parts of the intravaginal ring comprises active agent(s). Typically the intravaginal ring has a ring diameter of 50-60 mm. The diameter of body comprising the core and the membrane is typically 4.5-5.5 mm. The membrane typically has a thickness of 0.2-0.4 mm.

According to yet another embodiment the drug delivery device is produced by providing at least one cavity in the body of drug delivery device. Into this cavity material comprising an active agent is inserted. After that the adhesive material is applied on the cavity or in the cavity in order to fully cover the material with active agent. For example the cavity may be filled with the adhesive material. The cavity is then sealed by curing the adhesive material by radiation energy from the laser source. In this manner a permanent seal can be produced which provides a secure insertion of the material comprising the (therapeutically) active agent into the body of the drug delivery device. After application of the adhesive material, but before curing, any surplus adhesive material is removed, whereby the surface of the drug delivery device remains smooth and flat also over the sealed cavity.

According to further embodiment of the invention the adhesive material is applied on at least one distal end of the body of the drug delivery device and the distal end is sealed by curing the adhesive material by subjecting it to radiation energy from a laser source. Thus it is possible to seal off the distal end. Adhesive material can be applied also to two or more ends of the drug delivery device in order to seal them off. When the drug delivery device is, for example, an implant or a capsule used in an intrauterine system, the adhesive material can be applied on the both ends of the implant or the capsule, which contains the (therapeutically) active agent. After application of the adhesive material, but before curing, any surplus adhesive material is removed, whereby the surface of the drug delivery device remains smooth and flat also over the sealed distal end. After curing with laser radiation the adhesive material seals the ends of the implant or capsule. Sealing of the end may have a positive impact in particular on the initial release of the active agent and possibly reduce the initial burst of the (therapeutically) active agent(s) through the ends of the implant or capsule. The initial release may be a problem if the release controlling membrane does not cover the ends, for example if the implant or capsule is formed by cutting. This problem can now be solved without major negative impact on speed of manufacture of drug delivery devices.

According to yet further embodiment of the invention the adhesive material is arranged between the adjacent body parts and cured by using radiative energy from a laser, whereby a cured sealing layer is formed between the adjacent first and second body parts. The sealing layer prevents or controls the diffusion of the (therapeutically) active agent from the first body part to the second body part and/or vice versa. Thus it is possible to manufacture a drug delivery device, which comprises several different active agents and/or therapeutically active agents at different parts of its body. Because the (therapeutically) active agents can be sealed off from each other in different parts of the body, it possible to incorporate into one drug delivery device such (therapeutically) active agents, which might otherwise be incompatible with each other. Fluorosilicones are preferable adhesive materials if a formation of a sealing layer between body parts is desired.

In general, the present invention makes it possible to manufacture a drug delivery device where all the body parts comprise the same (therapeutically) active agent, but the body parts are different from each other in form of core and/or membrane structure or composition. Thus it is possible to produce drug delivery devices, where the diffusion profile of the active agent controllably varies over the body of the drug delivery device, for example in length direction or in different sections of the ring-like body.

As described above the body or body part of the drug delivery device preferably comprises a core. Poly(disubstituted) siloxanes, where the substituents are lower alkyl, preferably alkyl groups of 1 to 6 carbon atoms or phenyl groups are preferred as core and/or membrane materials. The said alkyl or phenyl may be substituted or unsubstituted. According to one embodiment of the invention the siloxane-based elastomer of the body is selected from the group comprising poly(dimethylsiloxane) (PDMS); siloxane-based elastomers comprising 3,3,3 trifluoropropyl groups attached to the silicon atoms of the siloxane units (fluoro-modified polysiloxanes); siloxane-based elastomers comprising poly(alkylene oxide) groups, where the poly(alkylene oxide) groups are present as alkoxy-terminated grafts or blocks linked to the polysiloxane units by silicon-carbon bonds or as a mixture of these forms. Suitable polysiloxanes and modified polysiloxane elastomers are described, for example, in EP 0652738 B1, WO 00/29464 and WO 00/00550. Among siloxane-based elastomers comprising poly(alkylene oxide) groups, polyethylene oxide block-polydimethylsiloxane copolymer (PEO-b-PDMS) is preferred. According to one preferable embodiment the siloxane-based elastomer is poly(dimethylsiloxane) (PDMS) or trifluoropropyl modified silica as described above. In general, polysiloxanes are physiologically inert and have also required mechanical properties.

According to a preferable embodiment of the invention, the core material is a siloxane-based elastomer, where from 1 to approximately 50% of the substituents attached to the silicon atoms of the siloxane units are 3,3,3-trifluoropropyl groups. The percentage of the substituents that are 3,3,3-trifluoropropyl groups may be, for example, in the range of 5-40%, preferably in the range of 10-35%. Alternatively the percentage of the substituents that are 3,3,3-trifluoropropyl groups may be 1-29% or 15-49.5%. The term "approximately 50%" means that the degree of 3,3,3-trifluoropropyl substitution is in fact somewhat below 50%, because the polymer contains a certain amount, about 0.15% of the substituents, of cross-linkable groups such as vinyl or vinyl-terminated groups.

The methods for the preparation of suitable polymers are given for example in International Patent Applications WO 00/00550, WO 00/29464 and WO 99110412.

The elastomeric core material may also comprise suitable additives, for example inert fillers or colourants, such as titanium dioxide or silica. The amount of the silica filler may be 0.1-40 weight-%. The amount of the titanium dioxide filler may be 0.1-5 weight-%. The particle size of the filler is typically 5-30 nm.

The above-listed siloxane-based elastomers are also suitable for use as adhesive material. The adhesive material may also comprise additives, such as fillers or colourants, as described above. For example, the colourant in the adhesive material makes it easy to localise the sealing layer or connection formed from the adhesive material.

As described above the body or body part of the drug delivery device preferably comprises a membrane enclosing or surrounding the above described core. In general, the same materials are suitable for use as the membrane material as disclosed above for the core material. Membrane and core can essentially consist of a same or different elastomer composition.

The elastomer composition used in the membrane is preferably such that it allows the predetermined, constant release rate(s) of the active agents and/or therapeutically active agent(s). The thickness of the membrane depends on materials and active agents used as well as on desired release profiles, but generally the thickness of the membrane is smaller than the thickness of the core.

The membrane may be arranged to cover the whole core or cover only a part of the core, depending on a number of factors, for example such as the choice of materials and the choice of active agents.

The membrane may comprise more than one layer. Each layer has a certain thickness, and the thickness of the layers may be the same or different. The combination of different membrane layers either in thickness or in material or both, gives a further possibility for controlling the release rates of the active agents.

As described above the body or body part of the drug delivery device may comprise at least one active agent. Any active agent and/or therapeutically active agent which is capable of diffusing the surface of the drug delivery device can be incorporated into the body of the drug delivery device. The active agent may be selected from the group comprising progestins, estrogens, aromatase inhibitors and non-steroidal anti-inflammatory drugs (NSAID).

The active agent(s) may be selected from group comprising progestins; chlormadinone acetate (CMA); norgestimate (NGM); norelgestromin (NGMN); norethisterone (NET)/norethisterone acetate (NETA); etonogestrel (3-keto-desogestrel); nomegestrol acetate (NOMAc); demegestone; promegestone; drospirenone (DRSP); medroxyprogesterone acetate (MPA); cyproterone acetate (CPA); trimegestone (TMG); levonorgestrel (LNG); norgestrel (NG); desogestrel (DSG); gestodene (GSD) and dienogest (DNG). Levonorgestrel (LNG); desogestrel (DSG); gestodene (GSD) and dienogest (DNG) are being preferred.

According to one embodiment natural and synthetic estrogens, especially estradiol or its esters, for example estradiol valerate or other conjugated estrogens (CEEs=conjugated equine estrogens) are preferred as estrogens. Particularly preferable are ethinylestradiol and estrogen or their esters such as estradiol valerate or benzoate.

According to one embodiment the therapeutically active agent may be selected from the group of selective aromatase inhibitors such as anastrozole (Arimidex®); exemestane (Aromasin®); fadrozole (Afema®); formestane (Lentaron®); letrozole (Femara®); pentrozole; vorozole (Rivizor®); and pharmaceutical acceptable salts thereof which are suitable for use as aromatase inhibitor. Anastrozole is being preferred.

According to one embodiment the therapeutically active agent may be selected from the group of non-selective Cox inhibitors as well as selective Cox 2 inhibitors are equally suitable as non-steroidal anti-inflammatory drugs (NSAID). Meloxicam, piroxicam, naproxen, celecoxib, diclofenac, tenoxicam, nimesulide, lornoxicam and indomethacin are being preferred, and indomethacin is particularly preferred.

According to one embodiment the therapeutically active agent may be a peptide.

According to one preferable embodiment of the invention the drug delivery device is an intravaginal ring, implant or an intrauterine system and comprises at least one therapeutically active agent for treatment of female diseases or conditions or an active agent, which is a contraceptive agent.

According to one preferred embodiment of the invention the drug delivery device, such as implant or intravaginal ring, has a body which comprises a core and a membrane encasing the core. At least one (therapeutically) active agent is embedded into the siloxane-based elastomer matrix of the core. For example, the (therapeutically) active agent is mixed with the elastomer composition of the core, and processed to the desired shape by moulding, casting, extrusion, or other appropriate methods. One or more membrane layers may be applied onto the core according to known methods such as by mechanical stretching, swelling or dipping. A reference is made to the U.S. Pat. Nos. 3,832,252, 3,854,480 and 4,957,119.

EXPERIMENTAL

Some embodiments of the invention are more closely described in the following non limiting examples.

Test Materials Used

Two different elastomer rods were used in the tests:

Rod 1: white polydimethylsiloxane, PDMS, with 0.3 weight-% of $TiO_2$. Tubular rod with outer diameter of 5.1 mm, inner diameter 2 mm.

Rod 2: transparent PDMS membrane with PDMS core containing 0.3 weight-% of $TiO_2$. Outer diameter of rod was 5 mm.

Lasers and Optical Setup Used 1.9 µm and 1.5 µm fiber lasers were used in the experiments.

1.9 µm laser was IPG TLR-120-WC (TL15555) which is continuous wave thulium fiber laser. The wavelength is 1940 nm and maximum nominal output power 120 W.

1.5 µm laser used was IPG ELR-100-AC (TL16518) which is continuous wave erbium fiber laser. The wavelength is 1567 nm and maximum nominal output power 100 W.

With both lasers same optical setup was used to guide the laser beam, shown in FIG. 1.

The optical setup 1 comprised a laser collimator 2, a beam expander 3, an axicon lens 4 and a mirror 5. The size of the laser beam after collimator is 5.5 mm. The laser beam is guided from laser collimator 2 to the beam expander 3, which is used to reduce the laser beam further. The laser beam size after beam expander 3 is 1.4 mm/1.8 mm, depending on used expander set up. The reduced beam is then guided to the axicon lens 3, which is used to form the spot shaped beam into a ring shaped beam. The diameter D of the ring shaped beam depends on the distance between the axicon lens 4 and the mirror 5. The closer the axicon lens, the smaller the diameter. The thickness t of the ring shaped beam is half of the thickness db of the incoming beam to the lens (see FIG. 2). The mirror 5 reflects the ring shaped beam to the rod (not shown), which is arranged in connection with the mirror 5.

The mirror has an opening in the one side from which a jig can be placed inside of the mirror. The jig keeps the ends of the rod in place and also blocks the incoming beam so that the beam does not effect to a wrong place on the rod.

Technical data of the parts of the optical setup:

Beam expander from Edmund Optics, Inc. (1-4×, Output Clear Aperture 28 mm, 1550 nm, Zoom Beam Expander)

Figure 2:
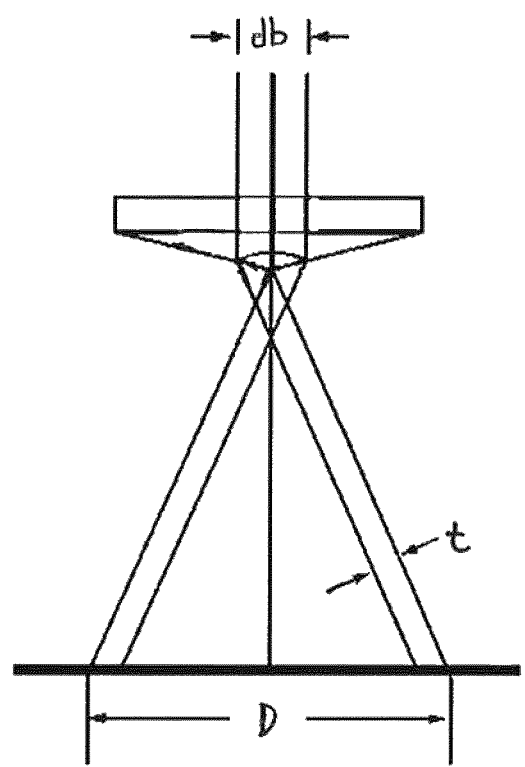
FIG. 2 is a schematic view of an axicon lens.

Axicon lens from Thorlabs, Inc. (AX2520-C). A schematic drawing of the axicon lens is shown in FIG. 2.

Mirror from Kugler GmbH.

Laser power of both lasers was measured after collimator and after the expander. It was estimated that the actual power on target rod was around 10-20% smaller than measured values due to the losses caused by optical setup.

Tensile Strength Equipment

The attached rods were tested for tensile strength. Used instrument was Lloyd Instrument LR5KPlus 5 kN Universal Materials Testing Machine (TL14002). Testing speed was 40 mm/min.

Results

Various joining times and laser powers were tested with both lasers and both test material rods. 0.9 mm beam width was used. The tensile strength of the obtained connection was then measured. The tested parameters and obtained results are shown in Table 1.

TABLE 1

Used parameters and obtained results.

| Laser | Material | Joining time [s] | Laser power [W] | Tensile strength [N] |
|---|---|---|---|---|
| 1.9 μm | Rod 1 | 1.0 | 89 | 86 |
| 1.9 μm | Rod 1 | 0.9 | 100 | 76 |
| 1.9 μm | Rod 1 | 0.75 | 95 | 32 |
| 1.9 μm | Rod 2 | 1.4 | 100 | 39 |
| 1.9 μm | Rod 2 | 1.2 | 100 | 22 |
| 1.9 μm | Rod 2 | 1.0 | 100 | 15 |
| 1.5 μm | Rod 1 | 1.4 | 111 | 86 |
| 1.5 μm | Rod 1 | 1.2 | 111 | 69 |
| 1.5 μm | Rod 1 | 1.0 | 111 | 42 |
| 1.5 μm | Rod 2 | 1.8 | 111 | 37 |
| 1.5 μm | Rod 2 | 1.6 | 111 | 36 |
| 1.5 μm | Rod 2 | 1.4 | 111 | 28 |

From results shown in Table 1 it is seen that a connection with good tensile strength can be obtained.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for producing a ring-shaped drug delivery device, which has a body comprising a siloxane-based elastomer and at least one active agent, the method comprising:
    obtaining an elongated body,
    forming the elongated body into a ring-like form by bringing its first end and the second end into close vicinity of each other,
    applying adhesive material between the first end and second end of the body, wherein the adhesive material comprises non-cured siloxane-based elastomer, and
    curing the adhesive material by subjecting it to radiation energy from a laser beam of a laser source which attaches the ends irrevocably together;
    wherein a mirror is used to reflect and guide the laser beam from the laser source to the adhesive material between the first end and the second end of the body,
    wherein the mirror has an opening on one side, and wherein a jig is used to keep the first end and the second end of the body in place and the jig is placed inside the mirror at the opening to keep the ends of the body of the device in place, and
    wherein the siloxane-based elastomer is polyethylene oxide block-polydimethylsiloxane copolymer (PEO-b-PDMS), poly(dimethylsiloxane) (PDMS) or trifluoropropyl modified silica.

2. The method according to claim 1, further comprising:
    providing at least one cavity into the body of drug delivery device,
    inserting material comprising an active agent into the cavity,
    applying adhesive material on the cavity, and
    sealing the cavity by curing the adhesive material by radiation energy from the laser source.

3. The method according to claim 1, further comprising increasing the temperature in the adhesive material to be cured to a temperature of at least 150° C. with the radiation energy from the laser source.

4. The method according to claim 1, further comprising applying the adhesive agent in amount that provides a connection with a width in the range of 0.1-15 mm.

5. The method according to claim 1, wherein the adhesive material is the same as the siloxane-based elastomer used for the body of the drug delivery device.

6. The method according to claim 1, further comprising using adhesive material, which comprises a peroxide initiator, which forms radicals when subjected to radiation energy from the laser source.

7. The method according to claim 1 wherein the drug delivery device is an implant or an intravaginal ring.

8. The method according to claim 1, wherein the drug delivery device further comprises anastrozole or levonorgestrel as an active agent.

9. The method according to claim 1, wherein the body of the device comprises a core and a membrane encasing the core.

10. The method according to claim 3, wherein said temperature is at least 200° C.

11. The method according to claim 4, wherein said width is in a range of 0.5-10 mm.

12. The method according to claim 4, wherein said width is in a range of 0.5-1.5 mm.

13. The method according to claim 1, wherein the at least one active agent is selected from the group consisting of progestins, estrogens, aromatase inhibitors and non-steroidal anti-inflammatory drugs (NSAID).

14. The method according to claim 1, wherein the laser source produces radiation energy having a wavelength in the range of 1100-2000 nm and/or the output power of laser is in the range of 20-200 W.

15. The method according to claim 1, wherein the adhesive material is subjected to the radiation energy for 0.2-5 seconds.

16. The method according to claim 1, wherein the adhesive material comprises a peroxide initiator or a noble metal catalyst.

* * * * *